(12) United States Patent
Lazewatsky

(10) Patent No.: US 6,808,698 B1
(45) Date of Patent: Oct. 26, 2004

(54) METHOD FOR LOCALIZATION OF BLOOD CLOTS

(75) Inventor: Joel Lazewatsky, Auburndale, MA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 09/534,893

(22) Filed: Mar. 24, 2000

Related U.S. Application Data

(60) Provisional application No. 60/126,359, filed on Mar. 26, 1999.

(51) Int. Cl.[7] ............................................. A61K 49/00
(52) U.S. Cl. ..................... 424/9.1; 424/1.11; 424/1.65; 424/1.69; 424/9.4; 534/14
(58) Field of Search ................... 424/1.11, 1.65, 424/1.69, 9.1, 9.3, 9.4, 9.5, 9.6, 9.7, 9.8; 534/7, 10–16; 514/2, 9

(56) References Cited

U.S. PATENT DOCUMENTS

| | | | |
|---|---|---|---|
| 4,427,646 A | 1/1984 | Olexa et al. | |
| 4,578,079 A | 3/1986 | Ruoslahti et al. | ............. 623/11 |
| 4,792,525 A | 12/1988 | Ruoslahti et al. | ..... 435/240.243 |
| 5,086,069 A | 2/1992 | Klein et al. | |
| 5,217,705 A | 6/1993 | Reno et al. | |
| 5,270,030 A | 12/1993 | Vogel et al. | |
| 5,279,812 A | 1/1994 | Krstenansky et al. | |
| 5,744,120 A | 4/1998 | Edwards et al. | |
| 5,750,088 A | 5/1998 | Sworin et al. | |
| 5,879,657 A | 3/1999 | DeGrado et al. | |
| 5,879,659 A | 3/1999 | Edwards et al. | |

FOREIGN PATENT DOCUMENTS

| | | |
|---|---|---|
| EP | 0 410 537 A1 | 1/1991 |
| EP | 0 410 539 A1 | 1/1991 |
| EP | 0 410 541 A1 | 1/1991 |
| EP | 0 422 937 A1 | 4/1991 |
| EP | 0 422 938 A1 | 4/1991 |
| EP | 0 425 212 A2 A3 | 5/1991 |
| EP | 0478328 | 1/1992 |
| EP | 0 569 132 A1 | 11/1993 |
| GB | 2 268 494 A | 1/1994 |
| WO | WO 89/05150 | 6/1989 |
| WO | WO 89/10135 | 11/1989 |
| WO | 9000178 | 1/1990 |
| WO | 9003391 | 4/1990 |
| WO | 9015818 | 12/1990 |
| WO | WO 91/01331 | 2/1991 |
| WO | WO 91/15515 | 10/1991 |
| WO | 9213572 | 8/1992 |
| WO | 9323085 | 11/1993 |
| WO | 9422494 | 10/1994 |
| WO | WO 96/31243 | 10/1996 |
| WO | Wo 96/40637 | 12/1996 |

OTHER PUBLICATIONS

Edwards, et al., Mar. 1, 1997, Bioconjugate Chemistry, 8, 2, 146–154.

Rajopadhye et al., Apr. 22, 1997, Bioorganic & Medicinal Chemistry Letters, 7, 8, 955–960.

(List continued on next page.)

Primary Examiner—Dameron L. Jones
(74) Attorney, Agent, or Firm—Paul D. Golian; Woodcock Washburn

(57) ABSTRACT

A method wherein a radiolabelled compound is localized at a thrombus. Two-dimensional images, representing a physical property associated with the radiolabelled thrombus, are acquired and assembled into a three-dimensional matrix of data. The three-dimensional matrix of data is then scanned along an array of parallel lines to determine a maximum value along each line. The maximum value along each line is then assigned to a pixel in a two-dimensional array, where the relative position of the pixel in the two-dimensional array corresponds to the relative position of the line in the array of parallel lines.

13 Claims, 1 Drawing Sheet

OTHER PUBLICATIONS

Barrett et al., 1997, Bioconjugate Chemistry, 8, 2, 155–160.
Liu et al., 1996, Bioconjugate Chemistry, 7, 1, 63–71.
Harris et al., Aug. 6, 1996, Bioorganic & Medicinal Chemistry, 6, 15, 1741–1746.
Hom et al, Aug. 1, 1997, Nuclear Medicine and Biology, 24, 6, 485–498.
Ojima et. al., 204th Meeting of the Amer. Chem. Soc., 1992, Abstract 44.
Hartman et. al., J. Med. Chem., 1992, 35, 4640.

METHOD FOR LOCALIZATION OF BLOOD CLOTS

This application claims the benefit of U.S. Provisional Application No. 60/126,359 filed on Mar. 26, 1999.

FIELD OF THE INVENTION

The present invention relates to a medical diagnostic method and, in particular, to an in vivo diagnostic method for detecting a blood clot, such as a pulmonary embolism or a thrombus, employing a radiopharmaceutical contrast agent and volume rendering of single photon emission computed tomography (SPECT) images.

BACKGROUND OF THE INVENTION

Pulmonary embolism is a condition of the lung that emerges when a portion of a blood clot (i.e., thrombus) growing pathologically within a patient breaks off (i.e., embolizes) and travels to the lung. In many instances, the condition itself is immediately life-threatening. However, even when the condition is not immediately life-threatening, a patient presenting with symptoms characteristic of pulmonary embolism must be properly diagnosed to assure that the symptoms do not represent other diseases. Accordingly, detection and localization of pulmonary embolism are critical to insure that the patient receives the appropriate care.

Previously, a technique for diagnosing tumors has been developed. The technique involves localizing a contrast agent at the tumor and obtaining a series of image slices of the tumor using single photon emission computed tomography (SPECT). The image slices are then individually inspected by a physician. As a result, the process is time consuming and expensive.

To improve the ability to diagnose tumors using SPECT, a volume rendering technique has been developed for displaying SPECT data derived from a complete set of image slices through the tumor. According to this technique, a three-dimensional matrix of data is assembled from the image slices. The three-dimensional matrix of data is then scanned along an array of parallel lines at a given angle with respect to the tumor. For each parallel line, the value of the most intense pixel along the parallel line is determined and assigned to a pixel in a two-dimensional array whose position corresponds to the position of the corresponding parallel line in the array of parallel lines. The process is repeated for a series of angles over 360° to produce a series of two-dimensional images. When the series of two-dimensional images are displayed sequentially, a rotating view of the most intense pixels is produced.

In spite of the foregoing, the utility of SPECT as a tool for diagnosing pulmonary embolism remained limited. The limited use of SPECT in connection with pulmonary embolism is due, at least in part, to the fact that the normal anatomy of the thorax is complex. As a result, structures highlighted by the contrast agent are variable, often in a pattern that is unfamiliar to physicians, and without the normal identifying landmarks. Thus, the location of the thrombus and the extent of disease was expected to be difficult to ascertain from the SPECT images, even if volume rendering techniques were employed.

Accordingly, it would be highly beneficial to provide a method for identification and localization of pulmonary embolism using SPECT wherein a three-dimensional representation of a thrombus is obtained. The three-dimensional representation of the thrombus should enable a physician to more clearly, accurately, and efficiently determine the extent of disease. Accordingly, the present invention should provide a significant qualitative improvement in the ability of a naive physician to identify and localize a thrombus.

SUMMARY OF THE INVENTION

The shortcomings associated with the known methods for localization of blood clots are overcome to a large degree by a method in accordance with the present invention. The method according to the present invention comprises the step of localizing a radiolabelled compound at a thrombus by administering a radiopharmaceutical compound to the patient. Two-dimensional images representing a physical property associated with the radiolabelled thrombus, such as single photon emission computed tomography (SPECT) images, are then acquired and assembled into a three-dimensional matrix of data. The three-dimensional matrix of data is then scanned along an array of parallel lines to determine a maximum value along each line. The maximum value along each line is then assigned to a pixel in a two-dimensional array, where the relative position of the pixel in the two-dimensional array corresponds to the relative position of the line in the array of parallel lines. The three-dimensional matrix of data is optionally scanned along additional arrays of parallel lines to produce a series of images of the thrombus as viewed from different angles. The series of images can be displayed sequentially to produce a rotating view of the thrombus.

BRIEF DESCRIPTION OF THE DRAWINGS

The foregoing summary, as well as the following detailed description of the preferred embodiments of the present invention, will be better understood when read in conjunction with the accompanying drawing, in which.

DETAILED DESCRIPTION OF PREFERRED EMBODIMENTS

Figure 1:
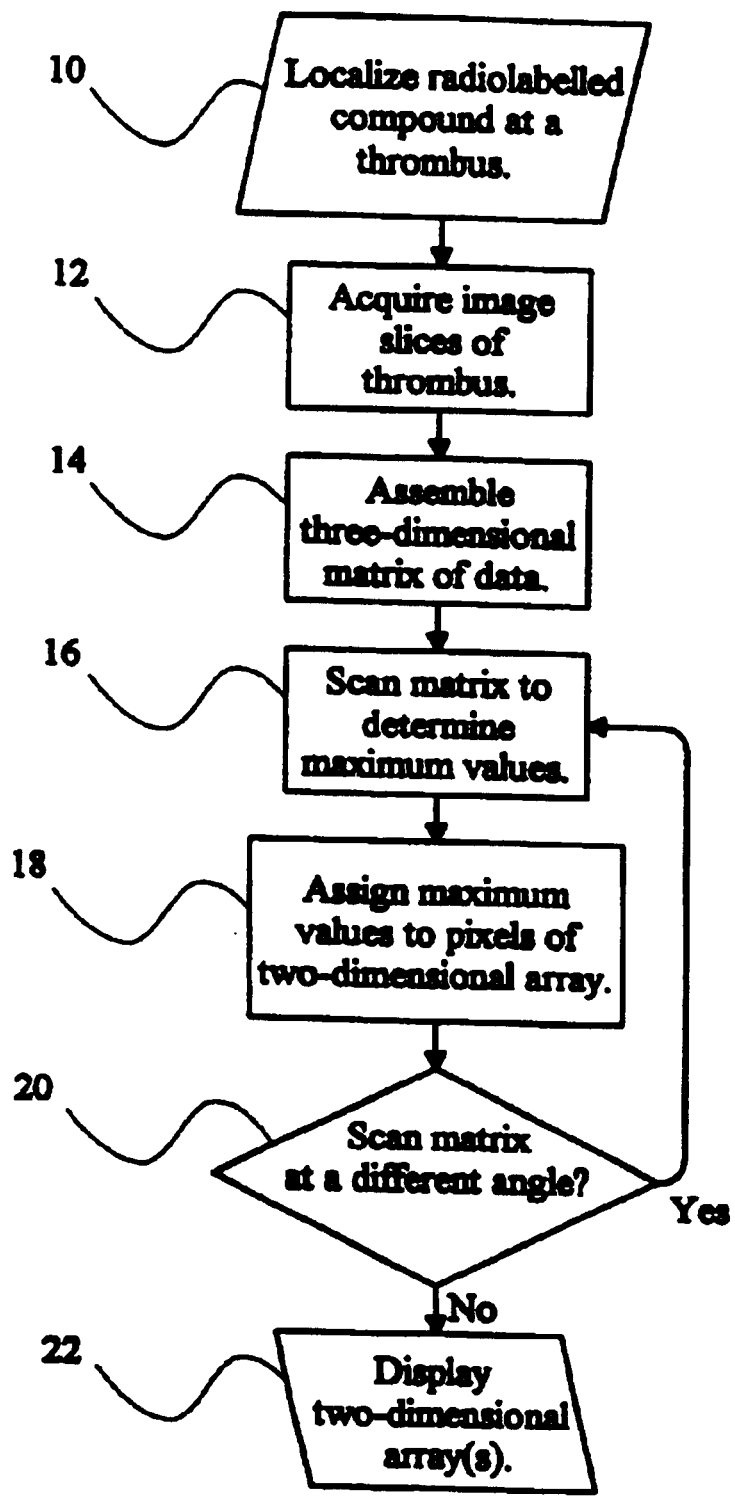
FIG. 1 is a flow chart depicting the steps of a method for imaging a thrombus in accordance with the present invention.

The present invention relates to a method for imaging a thrombus, the steps of which are depicted in FIG. 1. At step 10, the patient is administered a radiolabelled compound that preferentially binds to the thrombus. For example, the radiolabelled compound may be administered by injecting approximately 20 mCi (740 Mbq) of the radiolabelled compound into the venous circulation system of the patient. In one embodiment, the radiolabelled compound comprises a radiopharmaceutical of the type described in U.S. Pat. No. 5,744,120 issued Apr. 28, 1998 to Edwards et al., U.S. Pat. No. 5,879,657 issued Mar. 9, 1999 to DeGrado et al., U.S. Pat. No. 5,879,659 issued Mar. 9, 1999 to Edwards et al., and U.S. Pat. No. 5,750,088 issued May 12, 1998 to Sworin et al., all of which are incorporated herein by reference.

Specifically, a radiopharmaceutical useful as an imaging agent in accordance with the present invention is given by formula (I):

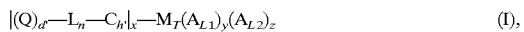

$$|(Q)_{d'}-L_n-C_h|_x-M_T(A_{L1})_y(A_{L2})_z \qquad (I),$$

wherein d' is preferably between about 1 and 20, x is independently 1–2; y is independently 1–2; and z is independently 0–4.

Q is a glycoprotein IIb/IIIA binding compound selected from the group including the cyclic IIb/IIIa receptor antagonist compounds described in co-pending U.S. Ser. No. 08/415,908,861 (equivalent to WO 94/22494); the RGD containing peptides described in U.S. Pat. Nos. 4,578,079 and 4,792,525, the patent applications PCT US88/04403, PCT US89/01742, PCT US90/03788, and PCT US91/02356, and by Ojima et. al., 204th Meeting of the Amer. Chem. Soc., 1992, Abstract 44; the peptides that are fibrinogen receptor antagonists described in European Patent Application Nos. 90202015.5, 90202030.4, 90202032.2, 90202032.0, 90311148.2, 90311151.6, and 90311537.6; the specific binding peptides and polypeptides described as IIb/IIIa receptor ligands, ligands for the polymerization site of fibrin, laminin derivatives, ligands for fibrinogen, or thrombin ligands in PCT NO 93/23085 (excluding the technetium binding groups); the oligopeptides that correspond to the IIIa protein described in PCT WO 90/00178; the hirudin-based peptides described in PCT WO 90/03391; the IIb/IIIa receptor ligands described in PCT WO 90/15818; the thrombus, platelet or atherosclerotic plaque binding peptides described in PCT WO 92/13572 (excluding the technetium binding group) and GB 9313965.7; the fibrin binding peptides described in U.S. Pat. Nos. 4,427,646 and 5,270,030; the hirudin-based peptides described in U.S. Pat. No. 5,279,812; the fibrin binding proteins described in U.S. Pat. No. 5,217,705; the guanine derivatives that bind to the IIb/IIIa receptor described in U.S. Pat. No. 5,086,069; the tyrosine derivatives described in European Patent Application No. 0478328A1, and Hartman et. al., J. Med. Chem., 1992, 35, 4640; or an oxidized low density lipoprotein (LDL).

In one embodiment, Q is of the formula (II):

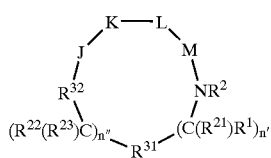

(II)

or a pharmaceutically acceptable salt or prodrug form thereof wherein:

$R^{31}$ is a $C_6$–$C_{14}$ saturated, partially saturated, or aromatic carbocyclic ring system substituted with 0–4 $R^{10}$ or $R^{10a}$;

$R^{32}$ is selected from:
—C(=O)—;
—C(=S)—;
—S(=O)$_2$—;
—S(=O)—;
—P(=Z)(ZR$^{13}$)—;

Z is S or O;

n" and n' are independently 0–2;

$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;

when n' is 2, $R^1$ or $R^{21}$ can alternatively be taken together with $R^1$ or $R^{21}$ on an adjacent carbon atom to form a direct bond, thereby to form a double or triple bond between said carbon atoms;

$R^{22}$ and $R^{23}$ can alternatively join to form a 3–7 membered carbocyclic ring substituted with 0–2 $R^{12}$;

when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;

$R^1$ and $R^2$, where $R^{21}$ is H, can alternatively join to form a 5–8 membered carbocyclic ring substituted with 0–2 $R^{12}$;

$R^{11}$ is selected from one or more of the following:
=O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy,
$C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, $C_3$–$C_6$ cycloalkoxy, $C_1$–$C_4$ alkyl (alkyl being substituted with 1–5 groups selected independently from:
—NR$^{13}$R$^{14}$, —CF$_3$, NO$_2$, —SO$_2$R$^{13a}$, or —S(=O)R$^{13a}$),
aryl substituted with 0–2 $R^{12}$,
a 5–10-membered heterocyclic ring system containing 1–4 heteroatoms independently selected from N, S, and O, said heterocyclic ring being substituted with 0–2 $R^{12}$;

$R^{12}$ is selected from one or more of the following:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), $C_3$–$C_6$ cycloalkoxy, —OC(=O)R$^{13}$, —C(=O)R$^{13}$, —OC(=O)OR$^{13a}$, —OR$^{13}$, —(C$_1$–C$_4$ alkyl)—OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, $C_2$–$C_6$ alkoxyalkyl, methylenedioxy, ethylenedioxy, $C_1$–$C_4$ haloalkyl, $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, $C_1$–$C_4$ alkyl (alkyl being substituted with —N(R$^{13}$)$_2$, —CF$_3$, NO$_2$, or —S(=O)R$^{13a}$);

$R^{13}$ is selected independently from: H, $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;

$R^{13a}$ is $C_1$–$C_{10}$ alkyl, $C_3$–$C_{10}$ cycloalkyl, $C_4$–$C_{12}$ alkylcycloalkyl, aryl, —(C$_1$–C$_{10}$ alkyl)aryl, or $C_3$–$C_{10}$ alkoxyalkyl;

when two $R^{13}$ groups are bonded to a single N, said $R^{13}$ groups may alternatively be taken together to form —$(CH_2)_{2-5}$— or —$(CH_2)O(CH_2)$—;

$R^{14}$ is OH, H, $C_1$–$C_4$ alkyl, or benzyl;

$R^{21}$ and $R^{23}$ are independently selected from:
  hydrogen;
  $C_1$–$C_4$ alkyl, optionally substituted with 1–6 halogen;
  benzyl;

$R^2$ is H or $C_1$–$C_8$ alkyl;

$R^{10}$ and $R^{10a}$ are selected independently from one or more of the following:
  phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_5$ alkoxy, —$CO_2R^{13}$, —$C(=O)N(R^{13})_2$, —$C(=O)NHOR^{13a}$, —$C(=O)NHN(R^{13})_2$, =$NOR^{13}$, —$B(R^{34})(R^{35})$, $C_3$–$C_6$ cycloalkoxy, —$OC(=O)R^{13}$, —$C(=O)R^{13}$, —$OC(=O)CR^{13a}$, —$OR^{13}$, —$(C_1$–$C_4$ alkyl)—$OR^{13}$, —$N(R^{13})_2$, —$OC(=O)N(R^{13})_2$, —$NR^{13}C(=O)R^{13}$, —$NR^{13}C(=O)OR^{13a}$, —$NR^{13}C(=O)N(R^{13})_2$, —$NR^{13}SO_2N(R^{13})_2$, —$NR^{13}SO_2R^{13a}$, —$SO_3H$, —$SO_2R^{13a}$, —$S(=O)R^{13a}$, —$SR^{13}$, —$SO_2N(R^{13})_2$, $C_2$–$C_6$ alkoxyalkyl, methylenedioxy, ethylenedioxy, $C_1$–$C_4$ haloalkyl (including —$C_vF_w$ where v=1 to 3 and w=1 to (2v+1)), $C_1$–$C_4$ haloalkoxy, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, $C_1$–$C_4$ alkyl (alkyl being substituted with —$N(R^{13})_2$, —$CF_3$, $NO_2$, or —$S(=O)R^{13a}$);

J is 3-aminopropionic acid or an L-isomer or D-isomer amino acid of structure —$N(R^3)C(R^4)(R^5)C(=O)$—, wherein:
  $R^3$ is H or $C_1$–$C_8$ alkyl;
  $R^4$ is H or $C_1$–$C_3$ alkyl;
  $R^5$ is selected from:
    hydrogen;
    $C_1$–$C_8$ alkyl substituted with 0–2 $R^{11}$;
    $C_2$–$C_8$ alkenyl substituted with 0–2 $R^{11}$;
    $C_2$–$C_8$ alkynyl substituted with 0–2 $R^{11}$;
    $C_3$–$C_{10}$ cycloalkyl substituted with 0–2 $R^{11}$;
    aryl substituted with 0–2 $R^{12}$;
    a 5–10-membered heterocyclic ring system containing 1–4 heteroatoms independently selected from N, S, or O, said heterocyclic ring being substituted with 0–2 $R^{12}$;
    =O F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —NHC(=NH)NHR^{13}, —C(=NH)NHR^{13}, =$NOR^{13}$, $NO_2$, —$C(=O)NHOR^{13}$, —$C(=O)NHNR^{13}R^{13a}$, =$NOR^{13}$, —$B(R^{34})(R^{35})$, —$OCH_2CO_2H$, 2-(1-morpholino)ethoxy, —$SC(=NH)NHR^{13}$, $N_3$, —$Si(CH_3)_3$, $(C_1$–$C_5$ alkyl)$NHR^{16}$;

—$(C_0$–$C_6$ alkyl)X;

where q is independently 0,1;

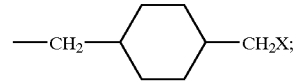

—$(CH_2)_mS(O)_{p'}(CH_2)_2X$, where m=1,2 and p'=0–2; wherein X is defined below; and $R^3$ and $R^4$ may also be taken together to form

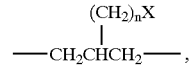

where n=0,1 and X is

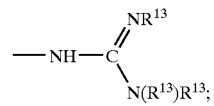

$R^3$ and $R^5$ can alternatively be taken together to form —$(CH_2)_t$— or —$CH_2S(O)_{p'}C(CH_3)_2$—, where t=2–4 and p'=0–2; or $R^4$ and $R^5$ can alternatively be taken together to form —$(CH_2)_u$—, where u=2–5;

$R^{16}$ is selected from:
  an amine protecting group;
  1–2 amino acids;
  1–2 amino acids substituted with an amine protecting group;

K is a D-isomer or L-isomer amino acid of structure —$(R^6)CH(R^7)C(=O)$—, wherein:
  $R^6$ is H or $C_1$–$C_8$ alkyl;
  $R^7$ is selected from:
    —$(C_1$–$C_7$ alkyl)X;

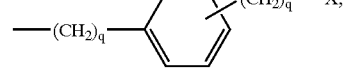

wherein each q is independently 0–2 and substitution on the phenyl is at the 3 or 4 position;

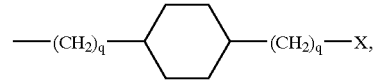

wherein each q is independently 0–2 and substitution on the cyclohexyl is at the 3 or 4 position;

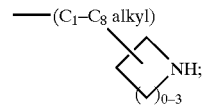

—$(CH_2)_mO$—$(C_1$–$C_4$ alkyl)—X, where m=1 or 2;

—(CH$_2$)$_m$S(O)$_{p'}$—(C$_1$–C$_4$ alkyl)—X, where m=1 or 2 and p'=0–2; and

X is selected from:

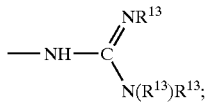

—N(R$^{13}$)R$^{13}$; —C(=NH)(NH$_2$); —SC(=NH)—NH$_2$; —NH—C(=NH)(NHCN); —NH—C(=NCN)(NH$_2$); —NH—C(=N—OR$^{13}$)(NH$_2$);

R$^6$ and R$^7$ can alternatively be taken together to form

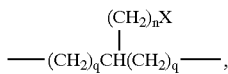

wherein each q is independently 1 or 2 and wherein n=0 or 1 and X is —NH$_2$ or

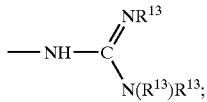

L is —Y(CH$_2$)$_v$C(=O)—, wherein:
Y is NH, N(C$_1$–C$_3$ alkyl), O, or S; and v=1 or 2;
M is a D-isomer or L-isomer amino acid of structure

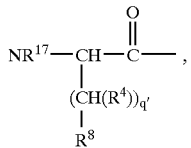

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$;

R$^{34}$ and R$^{35}$ are independently selected from:
—OH,
—F,
—N(R$^{13}$)$_2$, or
C$_1$–C$_8$-alkoxy;

R$^{34}$ and R$^{35}$ can alternatively be taken together form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O.

In another embodiment, Q is of the formula (III):

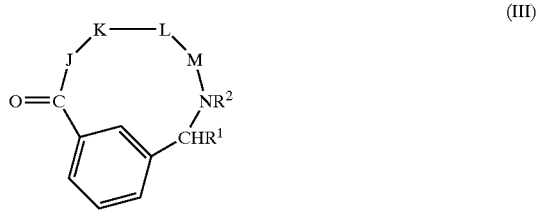

(III)

or a pharmaceutically acceptable salt or prodrug form thereof wherein:

the shown phenyl ring may be further substituted with 0–3 R$^{10}$;

R$^{10}$ is selected independently from: H, C$_1$–C$_8$ alkyl, phenyl, halogen, or C$_1$–C$_4$ alkoxy;

R$^1$ is H, C$_1$–C$_4$ alkyl, phenyl, benzyl, or phenyl-(C$_1$–C$_4$) alkyl;

R$^2$ is H or methyl;

R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

R$^{13a}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

when two R$^{13}$ groups are bonded to a single N, said R$^{13}$ groups may alternatively be taken together to form —(CH$_2$)$_{2-5}$— or —(CH$_2$)O(CH$_2$)—;

R$^{14}$ is OH, H, C$_1$–C$_4$ alkyl, or benzyl;

J is β-alanine or an L-isomer or D-isomer amino acid of structure —N(R$^3$)C(R$^4$)(R$^5$)C(=O)—, wherein:

R$^3$ is H or CH$_3$;

R$^4$ is H or C$_1$–C$_3$ alkyl;

R$^5$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, (CH$_2$)$_s$NH$_2$, —(CH$_2$)$_s$NHC(=NH)(NH$_2$), —(CH$_2$)$_s$NHR$^{16}$, where s=3–5; or R$^{16}$ is selected from:
an amine protecting group;
1–2 amino acids; or
1–2 amino acids substituted with an amine protecting group;

R$^3$ and R$^5$ can alternatively be taken together to form —CH$_2$CH$_2$CH$_2$—; or R$^4$ and R$^5$ can alternatively be taken together to form —(CH$_2$)$_u$—, where u=2–5;

K is an L-isomer amino acid of structure —N(R$^6$)CH(R$^7$)C(=O)—, wherein:

R$^6$ is H or C$_1$–C$_8$ alkyl;

R$^7$ is:

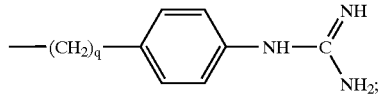

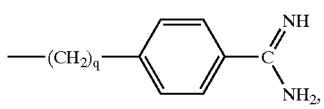

where q=0 or 1;
—(CH$_2$)$_r$X, where r=3–6;

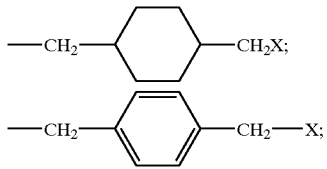

—(CH$_2$)$_m$S(CH$_2$)$_2$X, where m=1 or 2;
—(C$_3$–C$_7$ alkyl)—NH—(C$_1$–C$_6$ alkyl);

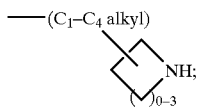

—(CH$_2$)$_m$—O—(C$_1$–C$_4$ alkyl)—NH—(C$_1$–C$_6$ alkyl), where m=1 or 2;
—(CH$_2$)$_m$—S—(C$_1$–C$_4$ alkyl)—NH—(C$_1$–C$_6$ alkyl), where m=1 or 2; and X is —NH$_2$ or —NHC(=NH)(NH$_2$), provided that X is not —NH$_2$ when r=4; or R$^6$ and R$^7$ are alternatively be taken together to form

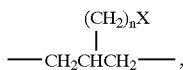

where n=0,1 and X is —NH$_2$ or —NHC(=NH)(NH$_2$);
L is —Y(CH$_2$)$_v$C(=O)—, wherein:
Y is NH, O, or S; and v=1,2;
M is a D-isomer or L-isomer amino acid of structure

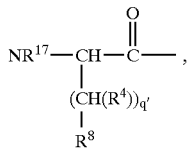

wherein:
q' is 0–2;
R$^{17}$ is H, C$_1$–C$_3$ alkyl;
R$^8$ is selected from:
—CO$_2$R$^{13}$, —SO$_3$R$^{13}$, —SO$_2$NHR$^{14}$, —B(R$^{34}$)(R$^{35}$), —NHSO$_2$CF$_3$, —CONHNHSO$_2$CF$_3$, —PO(OR$^{13}$)$_2$, —PO(OR$^{13}$)R$^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCOR$^{13}$, —CONHSO$_2$R$^{13a}$, —CH$_2$CONHSO$_2$R$^{13a}$, —NHSO$_2$NHCOR$^{13a}$, —NHCONHSO$_2$R$^{13a}$, —SO$_2$NHCONHR$^{13}$.

C$_{h'}$ is a radionuclide metal chelator or bonding unit bound to the biologically active compound Q, either directly or through the optional linking group L$_n$. C$_{h'}$ is preferably selected from the group consisting of: R$^{40}$N=N$^+$=, R$^{40}$R$^{41}$N—N=, R$^{40}$N=, and R$^{40}$N=N(H)—; wherein, R$^{40}$ is independently selected at each occurrence from the group consisting of: a bond to L$_n$, C$_1$–C$_{10}$ alkyl substituted with 0–3 R$^{52}$, aryl substituted with 0–3 R$^{52}$, cycloaklyl substituted with 0–3 R$^{52}$, heterocycle substituted with 0–3 R$^{52}$, heterocycloalkyl substituted with 0–3 R$^{52}$, aralkyl substituted with 0–3 R$^{52}$ and alkaryl substituted with 0–3 R$^{52}$;

R$^{41}$ is independently selected from the group consisting of: hydrogen, aryl substituted with 0–3 R$^{52}$, C$_1$–C$_{10}$ alkyl substituted with 0–3 R$^{52}$, and a heterocycle substituted with 0–3 R$^{52}$;

R$^{52}$ is independently selected at each occurrence from the group consisting of: a bond to L$_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, 2-(1-morpholino)ethoxy; and R$^{53}$, R$^{53a}$, and R$^{54}$ are each independently selected at each occurrence from the group consisting of: hydrogen, C$_1$–C$_6$ alkyl, and a bond to L$_n$.

In order to have a chelating diazenido group (i.e., a group of formula R$^{40}$N=N$^+$= or R$^{40}$N=(H)—) at least one other atom of the group located on R$^{40}$ must also be bound to the radionuclide. The atoms bound to the metal are termed donor atoms.

The optional linking group L$_n$ is given by the formula:

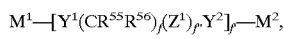

wherein:

M$^1$ is —[(CH$_2$)$_g$Z$^1$]$_{g'}$—(CR$^{55}$R$^{56}$)$_{g''}$—;

M$^2$ is —(CR$^{55}$R$^{56}$)$_{g''}$—[Z$^1$(CH$_2$)$_g$]$_{g'}$—;

g is independently 0–10;

g' is independently 0–1;

g" is independently 0–10;

f is independently 0–10;

f' is independently 0–10;

f" is independently 0–1;

Y$^1$ and Y$^2$, are independently selected at each occurrence from: a bond, O, NR$^{56}$, C=O, C(=O)O, OC(=O)O, C(=O)NH—, C=NR$^{56}$, S, SO, SO$_2$, SO$_3$, NHC(=O), (NH)$_2$C(=O), and (NH)$_2$C=S;

Z$^1$ is independently selected at each occurrence from a C$_6$–C$_{14}$ saturated, partially saturated, or aromatic carbocyclic ring system, substituted with 0–4 R$^{57}$; and a heterocyclic ring system, substituted with 0–4 R$^{57}$;

R$^{55}$ and R$^{56}$ are independently selected at each occurrence from the group consisting of: hydrogen; C$_1$–C$_{10}$ alkyl substituted with 0–5 R$^{57}$; and alkaryl wherein the aryl is substituted with 0–5 R$^{57}$;

R$^{57}$ is independently selected at each occurrence from the group: hydrogen, OH, NHR$^{58}$, C(=O)R$^{58}$, OC(=O)R$^{58}$, OC(=O)OR$^{58}$, C(=O)OR$^{58}$, C(=O)NR$^{58}$, C=N, $SR^{58}$, $SOR^{58}$, $SO_2R^{58}$, $NHC(=O)R^{58}$, NHC(=O)$NHR^{58}$, NHC(=S)$NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, C=$NR^{58}$, S, SO, $SO_2$, $SO_3$, NHC(=O), $(NH)_2C(=O)$, $(NH)_2C=S$; and $R^{58}$ is independently selected at each occurrence from the group: hydrogen; $C_1-C_6$ alkyl; benzyl, and phenyl.

The radiopharmaceutical compound used in accordance with the present invention is radiolabelled. By "radiolabelled", it is meant that the compound contains a radioisotope which is suitable for administration to a mammalian patient. Suitable radioisotopes are known to those skilled in the art and include, for example, isotopes of halogens (such as chlorine, fluorine, bromine and iodine), technetium and indium. Preferable radioisotopes include $^{123}I$, $^{125}I$, $^{131}I$, $^{99m}Tc$, and $^{111}In$, more preferably $^{111}In$, $^{123}I$ and $^{99m}Tc$, and most preferably $^{99m}Tc$. Radiolabelled compounds of the invention may be prepared using standard radiolabelling procedures well known to those skilled in the art. The glycoprotein IIb/IIIa binding compound, Q, is radiolabelled indirectly (that is, by incorporating the radiolabel into the compound through the chelating agent $C_{h'}$). Such radiolabelling should also be reasonably stable, both chemically and metabolically, applying recognized standards in the art. Also, although the radiolabelled compound may be labeled in a variety of fashions with a variety of different radioisotopes, as those skilled in the art will recognize, such radiolabelling should be carried out in a manner such that the high binding affinity and specificity of the unlabeled glycoprotein IIb/IIIa binding compound to the glycoprotein IIb/IIIa receptor is not significantly affected. By not significantly affected, it is meant that the binding affinity and specificity is not affected more than about 50%, preferably not more than about 40%, more preferably not more than about 30%, even more preferably not more than about 20%, and still even more preferably not more than about 10%, and most preferably the binding affinity and specificity is not affected at all.

Referring again to formula (I), $M_T$ is a transition metal radionuclide which is attached to the biologically active compound Q via the chelator $C_{h'}$. Preferred radiolabelled compounds of the invention are radiolabelled compounds wherein the radiolabel is located on the carbocyclic ring system of $R^{31}$ of formula (II). Even more preferred radiolabelled compounds of the invention are those of formula (III), wherein the radiolabel is located at position $R^{10}$ or $R^{10a}$ substituted on the benzene ring.

The coordination sphere of the radionuclide includes all the ligands or groups bound to the radionuclide. For a transition metal radionuclide, $M_t$, to be stable it typically has a coordination number comprised of an integer greater than or equal to 5 and less than or equal to 7; that is there are 5 to 7 atoms bound to the metal and it is said to have a complete coordination sphere. If the chelator or bonding unit $C_{h'}$ does not provide all of the atoms necessary to stabilize the metal radionuclide by completing its coordination sphere, the coordination sphere is completed by donor atoms from other ligands, termed ancillary or co-ligands, which can be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

The radiopharmaceuticals prepared from the reagents of the present invention can be comprised of one or two ancillary or co-ligands, designated $A_{L1}$, in a binary ligand system. The one or two ancillary or co-ligands, $A_{L1}$, comprising the radiopharmaceuticals can be independently selected from the group consisting of: dioxygen ligands, functionalized aminocarboxylates and halides; provided that the coordination sphere of the radionuclide is complete.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2 or 3,4 hydroxypyridinones, or pharmaceutically acceptable salts thereof.

Functionalized aminocarboxylates include ligands that have a combination of nitrogen and oxygen donor atoms. Examples include but are not limited to: iminodiacetic acid, 2,3 diaminopropionic acid, nitrilotriacetic acid, N,N'-ethylenediamine diacetic acid, N,N,N'-ethylenediamine triacetic acid, hydroxyethylethylenediamine triacetic acid, N,N'-ethylenediamine bis-hydroxyphenylglycine, or the ligands described in Eur. Pat. Appl. No. 93302712.0, or pharmaceutically acceptable salts thereof.

Halides which are suitable for use as the ancillary ligand $A_{L1}$ can be chloride, bromide, fluoride, iodide, or pharmaceutically acceptable salts thereof.

Of particular utility are radiopharmaceuticals prepared from the reagents of the present invention comprised of two different types of ancillary or co-ligands, one or two ligands designated the first ancillary or co-ligand or ligands, $A_{L1}$, and independently selected from the group: dioxygen ligands, functionalized aminocarboxylates and halides; and one to four ligands designated the second ancillary or co-ligand or ligands, $A_{L2}$, selected from the group: trisubstituted phosphines, trisubstituted arsines, tetrasubstituted diphosphines and tetrasubstituted diarsines, in a ternary ligand system. Radiopharmaceuticals comprised of one or more ancillary or co-ligands $A_{L2}$ are more stable compared to said radiopharmaceuticals that are not comprised of one or more ancillary ligands, $A_{L2}$; that is, they have a minimal number of isomeric forms, the relative ratios of which do not change significantly with time, and remain substantially intact upon dilution.

In one particular embodiment, the radiopharmaceutical comprises a compound of the formula (IV):

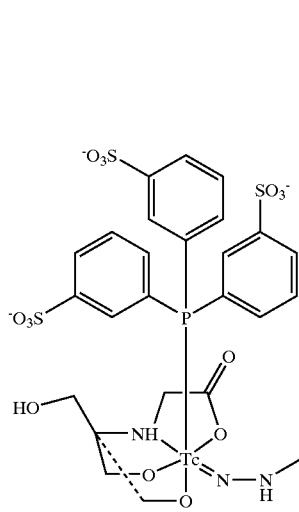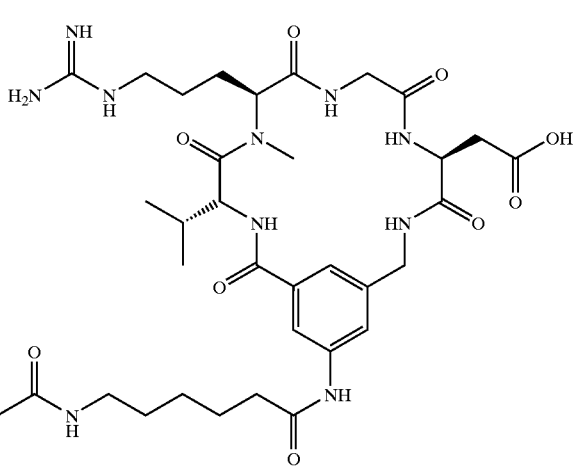

(IV).

In another particular embodiment, the radiopharmaceutical comprises a compound of the formula (V):

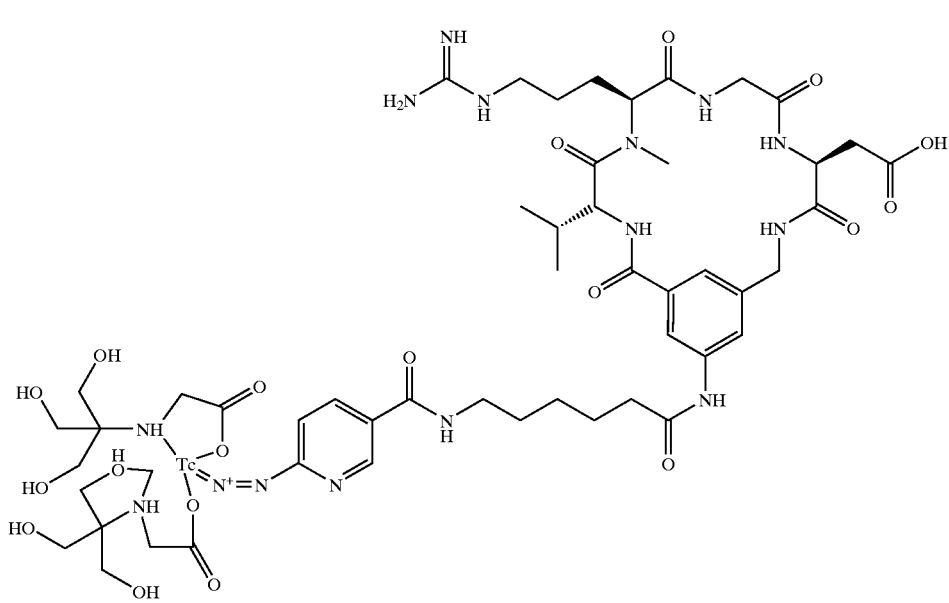

(V).

After the radiopharmaceutical has been administered, a series of image slices of the thrombus are acquired at step 12 of FIG. 1. The image slices reflect the concentration of radioactivity within the thrombus. Each image slice is composed of a two-dimensional array of pixels, wherein each pixel comprises an intensity value representative of the concentration of radioactivity at the particular position within the thrombus which corresponds to the pixel. In one embodiment, the image slices are obtained using a gamma camera to record single photon emission computed tomography (SPECT) images.

When the method of the present invention is used to detect an arterial thrombus, for example, data should be acquired using parameters that enhance the sensitivity of the technique for small lesions. In particular, when SPECT images are acquired, the parameters should include a 3 mm or smaller digital sampling (i.e., pixel size), and a minimum of 90 views over a 360 degree rotation or 45 views over a 190 degree rotation. Further, very high-resolution collimators and multiple heads should be used to increase the resolution and sensitivity, respectively. In addition, the acquired data should be reconstructed using a spatial filter with a relatively high frequency cutoff (i.e., approximately 3.00 or higher) to minimize resolution loss due to smoothing. A minimum of thirty angles ensures a visually smooth effect when the views are intended to be displayed sequentially to produce a rotating view of the thrombus, as described below.

At step 14, the image slices are reconstructed and assembled into a three-dimensional matrix of data. The three-dimensional matrix of data is assembled by stacking the individual image slices in sequential order. When the image slices are collected perpendicularly to the long axis of the patient, the three-dimensional matrix of data is organized as a series of transaxial image slices.

Once the three-dimensional matrix of data has been assembled, the matrix of data is scanned along an array of parallel lines (usually perpendicular to the vertical axis of the body), at step 16, to determine the maximum intensity value along each of the parallel lines. The maximum intensity value along a parallel line is equivalent to the most intense pixel within the matrix of data encountered along that parallel line. The most intense pixel is defined as the pixel corresponding to the position within the lesion where the radioactivity is most intense.

At step 18, the maximum value along each parallel line is assigned to a pixel in a two-dimensional image array. The relative position of the pixel in the two-dimensional image array corresponds to the relative position of the line in the array of parallel lines. The resulting two-dimensional image array therefore represents an image of the most intense pixels as viewed by an observer viewing the thrombus along the array of parallel lines.

The three-dimensional matrix of data can be scanned along additional arrays of parallel lines in order to produce image arrays of the thrombus from different angles. At step 20, it is determined whether the three-dimensional matrix of data is to be scanned at a different angle. If the matrix of data is to be scanned at a different angle, the matrix of data is scanned along the new angle at step 16. Preferably, the lesion is scanned along a minimum of 90 views over a series of angles over 360° or a minimum of 45 views over a series of angles over 180°.

If additional views of the thrombus are not desired, the results are displayed at step 22. The results can be displayed as individual views of the thrombus by displaying one or more of the individual two-dimensional image arrays. Alternatively, when two-dimensional image arrays at more than one angle have been obtained, the individual two-dimensional image arrays can be displayed sequentially by angle to produce a rotating view of the most intense pixels.

Although the above discussion has focused primarily on localization of pulmonary embolism, the present invention is not intended to be so limited. Instead, the present invention is intended to relate to any medical condition capable of diagnosis using a clot-binding radiopharmaceutical contrast agent and SPECT. For example, it is recognized that the present invention is equally applicable to localization of thrombii in general and arterial coronary thrombii in particular.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for imaging a pulmonary embolus comprising the steps of:

a. localizing a radiolabelled compound at the pulmonary embolus;

b. acquiring image slices representing the concentration of radioactivity within the radiolabelled pulmonary embolus;

c. assembling the image slices into a three-dimensional matrix of data;

d. scanning the three-dimensional matrix of data along an array of parallel lines to determine a maximum value alone each line; and e. assigning the maximum value along each line to a pixel in a two-dimensional array, the position of the pixel corresponding to the position of the line in the array of parallel lines;

wherein the localization step comprises the step of localizing a compound of the formula (I), and pharmaceutically acceptable salts thereof, at the pulmonary embolus:

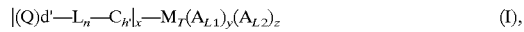

wherein,

Q is a glycoprotein IIb/IIIa binding compound;

d' is 1–20;

$L_n$ is a linking group of formula:

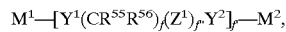

wherein:

$M^1$ is $—[(CH_2)_g Z^1]_{g'}—(CR^{55}R^{56})_{g''}—$;

$M^2$ is $—(CR^{55}R^{56})_{g''}—[Z^1(CH_2)_g]_{g'}—$;

g is 0;

g' is 0;

g" is 0;

f is 0;

f' is independently 0–10;

f" is independently 0–1;

$Y^1$ is a bond;

$Y^2$ is NHC(=O);

$Z^1$ is independently selected at each occurrence from a $C_6$–$C_{14}$ saturated, partially saturated, or aromatic carbocyclic ring system, substituted with 0–4 $R^{57}$; and a heterocyclic ring system, substituted with 0–4 $R^{57}$;

$R^{55}$ and $R^{56}$ are independently selected at each occurrence from: hydrogen; $C_1$–$C_{10}$ alkyl substituted with 0–5 $R^{57}$; and alkaryl wherein the aryl is substituted with 0–5 $R^{57}$;

$R^{57}$ is independently selected at each occurrence from the group: hydrogen, OH, $NHR^{58}$, $C(=O)R^{58}$, $OC(=O)R^{58}$, $OC(=O)OR^{58}$, $C(=O)OR^{58}$, $C(=O)NR^{58}$, $C\equiv N$, $SR^{58}$, $SOR^{58}$, $SO_2R^{58}$, $NHC(=O)R^{58}$, $NHC(=O)NHR^{58}$, $NHC(=S)NHR^{58}$; or, alternatively, when attached to an additional molecule Q, $R^{57}$ is independently selected at each occurrence from the group: O, $NR^{58}$, C=O, C(=O)O, OC(=O)O, C(=O)N—, $C=NR^{58}$, S, SO, $SO_2$, $SO_3$, NHC(=O), $(NH)_2C(=O)$, $(NH)_2C=S$; and, $R^{58}$ is independently selected at each occurrence from the group: hydrogen; $C_1$–$C_6$ alkyl; benzyl, and phenyl;

$M_T$ is a transition metal radionuclide;

$C_{h'}$ is a radionuclide metal chelator or bonding unit bound to the transition metal radionuclide of the formula $R^{40}R^{41}N—N=$;

$R^{40}$ is a heterocycle substituted with 1 $R^{52}$;

$R^{41}$ is independently selected from the group: hydrogen, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is a bond to $L_n$;

$A_{L1}$ is a first ligand wherein each of the y first ligands are functionalized aminocarboxylates;

$A_{L2}$ is a second ligand wherein each of the z second ligands are trisubstituted phosphines;

x is independently 1–2;

y is independently 1–2;

z is independently 0–4; and wherein Q is of the formula (II),

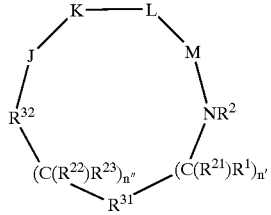
(II)

or a pharmaceutically acceptable salt or prodrug form thereof wherein:

$R^{31}$ is a $C_6$–$C_{14}$ aromatic carbocyclic ring system substituted with 1 $R^{10}$;

$R^{10}$ is —$NR^{13}C(=O)R^{13}$;

J is an L-isomer or D-isomer amino acid of structure —$N(R^3)C(R^4)(R^5)C(=O)$—, wherein:

$R^3$ is H or $C_1$–$C_8$ alkyl;

$R^4$ is H or $C_1$–$C_3$ alkyl;

$R^5$ is selected from:
hydrogen;
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, or O, said heterocyclic ring being substituted with 0–2 $R^{12}$;
=O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —$NHC(=NH)NHR^{13}$, —$C(=NH)NHR^{13}$, =$NOR^{13}$, $NO_2$, —$C(=O)NHOR^{13}$, —$C(=O)NHNR^{13}R^{13a}$, =$NOR^{13}$, —$B(R^{34})(R^{35})$, —$OCH_2CO_2H$, 2-(1-morpholino)ethoxy, —$SC(=NH)NHR^{13}$, $N_3$, —$Si(CH_3)_3$, ($C_1$–$C_5$ alkyl)$NHR^{16}$;

—($C_0$–$C_6$ alkyl)X;

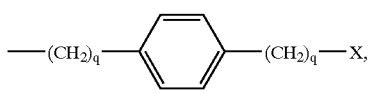

where q is independently 0,1;

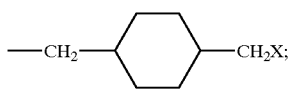

—$(CH_2)_mS(O)_{p'}(CH_2)_2X$, where m=1,2 and p'=0–2; and $R^3$ and $R^4$ may also be taken together to form

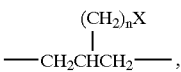

where n=0, 1 and X is

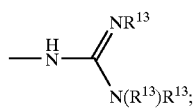

$R^3$ and $R^5$ can alternatively be taken together to form —$(CH_2)_t$— or —$CH_2S(O)_{p'}C(CH_3)_2$—, where t=2–4 and p'=0–2; or $R^4$ and $R^5$ can alternatively be taken together to form —$(CH_2)_u$—, where u=2–5;

$R^{16}$ is selected from:
an amine protecting group;
1–2 amino acids;
1–2 amino acids substituted with an amine protecting group;

K is a D-isomer or L-isomer amino acid of structure —$N(R^6)CH(R^7)C(=O)$—, wherein:

$R^6$ is H or $C_1$–$C_8$ alkyl;

$R^7$ is selected from:
—($C_1$–$C_7$ alkyl)X;

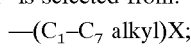
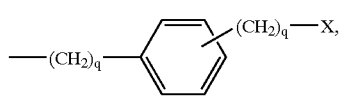

wherein each q is independently 0–2 and substitution on the phenyl is at the 3 or 4 position;

wherein each q is independently 0–2 and substitution on the cyclohexyl is at the 3 or 4 position;

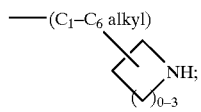

—$(CH_2)_mO$—($C_1$–$C_4$ alkyl)—X, where m=1 or 2;

—$(CH_2)_mS(O)_{p'}$—($C_1$–$C_4$ alkyl)—X, where m=1 or 2 and p'=0–2; and

X is selected from:

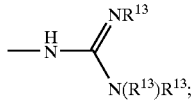

—N($R^{13}$)$R^{13}$; —C(=NH)(NH$_2$); —SC(=NH)—NH$_2$; —NH—C(=NH)(NHCN); —NH—C(=NCN)(NH$_2$); —NH—C(=N—O$R^{13}$)(NH$_2$);

$R^6$ and $R^7$ can alternatively be taken together to form

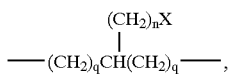

wherein each q is independently 1 or 2 and wherein n=0 or 1 and X is —NH$_2$ or

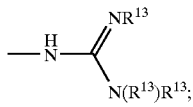

L is —Y(CH$_2$)$_v$C(=O)—, wherein Y is NH and v=1 or 2;
M is a D-isomer or L-isomer amino acid of structure

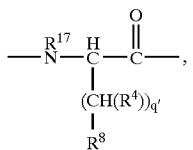

wherein:
q' is 0–2;
$R^{17}$ is H, $C_1$–$C_3$ alkyl;
$R^8$ is selected from:
—CO$_2$$R^{13}$, —SO$_3$$R^{13}$, —SO$_2$NH$R^{14}$, —B($R^{34}$)($R^{35}$), —NHSO$_2$CF$_3$, —CONHNHSO$_2$CF$_3$, —PO(O$R^{13}$)$_2$, —PO(O$R^{13}$)$R^{13}$, —SO$_2$NH-heteroaryl (said heteroaryl being 5–10-membered and having 1–4 heteroatoms selected independently from N, S, or O), —SO$_2$NH-heteroaryl (said heteroaryl being 5–10-membered and having 1–4 heteroatoms selected independently from N, S, or O), —SO$_2$NHCO$R^{13}$, —CONHSO$_2$$R^{13a}$, —CH$_2$CONHSO$_2$$R^{13a}$, —NHSO$_2$NHCO$R^{13a}$, —NHCONHSO$_2$$R^{13a}$, —SO$_2$NHCONH$R^{13}$;
$R^{34}$ and $R^{35}$ are independently selected from:
—OH,
—F,
N($R^{13}$)$_2$, or
$C_1$–$C_8$-alkoxy;
$R^{34}$ and $R^{35}$ can alternatively be taken together to form:
a cyclic boron ester where said chain or ring contains from 2 to 20 carbon atoms and, optionally, 1–4 heteroatoms independently selected from N, S, or O;
a divalent cyclic boron amide where said chain or ring contains from 2 to 20 carbon atoms and, optionally, 1–4 heteroatoms independently selected from N, S, or O;
a cyclic boron amide-ester where said chain or ring contains from 2 to 20 carbon atoms and, optionally, 1–4 heteroatoms independently selected from N, S, or O;

$R^{32}$ is —C(=O)—;
n" and n' are independently 0–2;
$R^1$ and $R^{22}$ are independently selected from the following groups:
hydrogen,
$C_1$–$C_8$ alkyl substituted with 0–2 $R^{11}$;
$C_2$–$C_8$ alkenyl substituted with 0–2 $R^{11}$;
$C_2$–$C_8$ alkynyl substituted with 0–2 $R^{11}$;
$C_3$–$C_{10}$ cycloalkyl substituted with 0–2 $R^{11}$;
aryl substituted with 0–2 $R^{12}$;
a 5–10-membered heterocyclic ring system containing 1–4 heteroatoms independently selected from N, S, and O, said heterocyclic ring being substituted with 0–2 $R^{12}$;
=O, F, Cl, Br, I, —CF$_3$, —CN, —CO$_2$$R^{13}$, —C(=O)$R^{13}$, —C(=O)N($R^{13}$)$_2$, —CHO, —CH$_2$O$R^{13}$, —OC(=O)$R^{13}$, —OC(=O)O$R^{13a}$, —O$R^{13}$, —OC(=O)N($R^{13}$)$_2$, —N$R^{13}$C(=O)$R^{13}$, —N$R^{14}$C(=O)O$R^{13a}$, —N$R^{13}$C(=O)N($R^{13}$)$_2$, —N$R^{14}$SO$_2$N($R^{13}$)$_2$, —N$R^{14}$SO$_2$$R^{13a}$, —SO$_3$H, —SO$_2$$R^{13a}$, —S$R^{13}$, —S(=O)$R^{13a}$, —SO$_2$N($R^{13}$)$_2$, —N($R^{13}$)$_2$, —NHC(=NH)NH$R^{13}$, —C(=NH)NH$R^{13}$, =NO$R^{13}$, NO$_2$, —C(=O)NHO$R^{13}$, —C(=O)NHN$R^{13}$$R^{13a}$, —OCH$_2$CO$_2$H, 2-(1-morpholino)ethoxy;

$R^1$ and $R^{21}$ can alternatively join to form a 3–7 membered carbocyclic ring substituted with 0–2 $R^{12}$;
when n' is 2, $R^1$ or $R^{21}$ can alternatively be taken together with $R^1$ or $R^{21}$ on an adjacent carbon atom to form a direct bond, thereby to form a double or triple bond between said carbon atoms;
$R^{22}$ and $R^{23}$ can alternatively join to form a 3–7 membered carbocyclic ring substituted with 0–2 $R^{12}$;
when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;
$R^1$ and $R^2$, where $R^{21}$ is H, can alternatively join to form a 5–8 membered carbocyclic ring substituted with 0–2 $R^{12}$;
$R^{11}$ is selected from one or more of the following:
=O, F, Cl, Br, I, —CF$_3$, —CN, —CO$_2$$R^{13}$, —C(=O)$R^{13}$, —C(=O)N($R^{13}$)$_2$, —CHO, —CH$_2$O$R^{13}$, —OC(=O)$R^{13}$, —OC(=)O$R^{13a}$, —O$R^{13}$, —OC(=O)N($R^{13}$)$_2$, —N$R^{13}$C(=O)$R^{13}$, —N$R^{14}$C(=O)O$R^{13a}$, —N$R^{13}$C(=O)N($R^{13}$)$_2$, —N$R^{14}$SO$_2$N($R^{13}$)$_2$, —N$R^{14}$SO$_2$$R^{13a}$, —SO$_3$H, —SO$_2$$R^{13a}$, —S$R^{13}$, —S(=O)$R^{13a}$, —SO$_2$N($R^{13}$)$_2$, —N($R^{13}$)$_2$, —NHC(=NH)NH$R^{13}$, —C(=NH)NH$R^{13}$, =NO$R^{13}$, NO$_2$, —C(=O)NHOR$^{13}$, —C(=O)NHNR$^{13}$R$^{13a}$, —OCH$_2$CO$_2$H, 2-(1-morpholino)ethoxy, C$_1$–C$_5$ alkyl, C$_2$–C$_4$ alkenyl, C$_3$–C$_6$ cycloalkyl, C$_3$–C$_6$ cycloalkylmethyl, C$_2$–C$_6$ alkoxyalkyl, C$_3$–C$_6$ cycloalkoxy, C$_1$–C$_4$ alkyl (alkyl being substituted with 1–5 groups selected independently from: —NR$^{13}$R$^{14}$, —CF$_3$, NO$_2$, —SO$_2$R$^{13a}$, or —S(=O)R$^{13a}$), aryl substituted with 0–2 R$^{12}$, a 5–10-membered heterocyclic ring system containing 1–4 heteroatoms independently selected from N, S, and O, said heterocyclic ring being substituted with 0–2 R$^{12}$;

R$^{12}$ is selected from one or more of the following: phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), C$_3$–C$_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, C$_2$–C$_6$ alkoxyalkyl, methylenedioxy, ethylenedioxy, C$_1$–C$_4$ haloalkyl, C$_1$–C$_4$ haloalkoxy, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, C$_1$–C$_4$ alkyl (alkyl being substituted with —N(R$^{13}$)$_2$, —CF$_3$, NO$_2$, or —S(=O)R$^{13a}$);

R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

R$^{13}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

when two R$^{113}$ groups are bonded to a single N, said R$^{13}$ group may alternatively be taken together to form —(CH$_2$)$_{2-5}$— or —(CH$_2$)O(CH$_2$)—;

R$^{14}$ is OH, H, C$_1$–C$_4$ alkyl, or benzyl;

R$^{21}$ and R$^{23}$ are independently selected from: hydrogen,

C$_1$–C$_4$ alkyl, optionally substituted with 1–6 halogen; and benzyl; and

R$^2$ is H or C$_1$–C$_8$ alkyl.

2. The method of claim 1 wherein M$_T$ is selected from the group consisting of: technetium-99m, rhenium-186, and rhenium-188.

3. The method of claim 1 wherein the localization step comprises the step of localizing a compound of the formula (IV) at the pulmonary embolus:

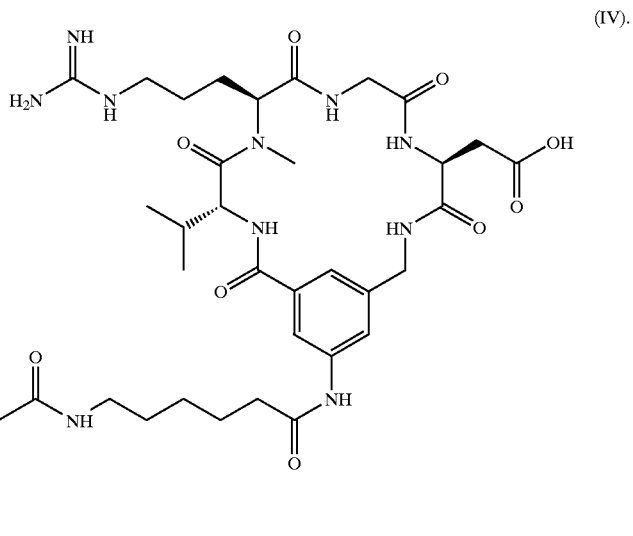

(IV).

4. The method of claim 1 wherein the acquisition step comprises the step of acquiring single photon emission computed tomography images of the pulmonary embolus.

5. The method of claim 1 wherein the acquisition step comprises the step of acquiring transaxial image slices and further comprising the step of reformatting the transaxial image slices into image slices that are parallel to a long axis associated with the pulmonary embolus.

6. The method of claim 1 comprising the step of displaying the two dimensional array as a reprojected image.

7. The method of claim 1 wherein the scanning step is performed at a series of angles.

8. The method of claim 7 wherein the assignment step is performed at each of the series of angles.

9. The method of claim 8 comprising the step of sequentially displaying the two-dimensional arrays as reprojected images.

10. The method of claim 1 comprising the step of displaying the two-dimensional array as a reprojected image.

11. The method of claim 1 wherein the scanning step is performed at a series of angles.

12. The method of claim 11 wherein the assignment step is performed at each of the series of angles.

13. The method of claim 12 comprising the step of sequentially displaying the two-dimensional arrays as reprojected images.

* * * * *